United States Patent [19]
Kletschka

[11] Patent Number: 5,195,877
[45] Date of Patent: Mar. 23, 1993

[54] FLUID PUMP WITH MAGNETICALLY LEVITATED IMPELLER

[76] Inventor: Harold D. Kletschka, 1925 Noble Dr., Minneapolis, Minn. 55422

[21] Appl. No.: 774,034

[22] Filed: Oct. 7, 1991

Related U.S. Application Data

[63] Continuation-in-part of Ser. No. 593,695, Oct. 5, 1990, Pat. No. 5,055,005.

[51] Int. Cl.$^5$ ............................................. F04B 17/00
[52] U.S. Cl. .................................... 417/356; 415/900; 600/16; 623/3
[58] Field of Search ......................... 417/356; 415/900; 600/16; 623/3

[56] References Cited

U.S. PATENT DOCUMENTS

| | | | |
|---|---|---|---|
| 3,957,389 | 5/1976 | Rafferty et al. | 415/900 X |
| 4,688,998 | 8/1987 | Olsen et al. | 415/900 X |
| 4,779,614 | 10/1988 | Moise | 415/900 X |
| 4,944,748 | 7/1990 | Bramm et al. | 623/3 |

Primary Examiner—Leonard E. Smith
Attorney, Agent, or Firm—Dorsey & Whitney

[57] ABSTRACT

A fluid pump with rotary impeller is disclosed which comprises an electromagnetically-driven, bearing-free, seal-free rotary impeller levitated by localized opposed, repulsive, permanent magnetic forces and by fluid forces, or by localized opposed repulsive magnetic forces only. Levitation by localized opposed magnetic or magnetic and fluid forces of an impeller driven by electromagnetic forces eliminates the need for bearings and seals in the driving mechanism. This avoids the heat build-up and leakage associated with other pumping mechanisms, which can be of importance in pumping of physiological fluids such as blood. The levitating forces of the present invention are applied repulsively both axially and radially with respect to the impeller and are auto-adjusting, such that any attempted displacement of the impeller will automatically incur a corrective change in levitating forces. The invention should be of use in numerous medical and non-medical applications where the benefits of impeller levitation by localized forces are apparent.

14 Claims, 5 Drawing Sheets

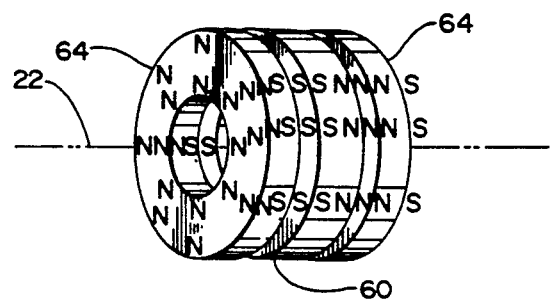
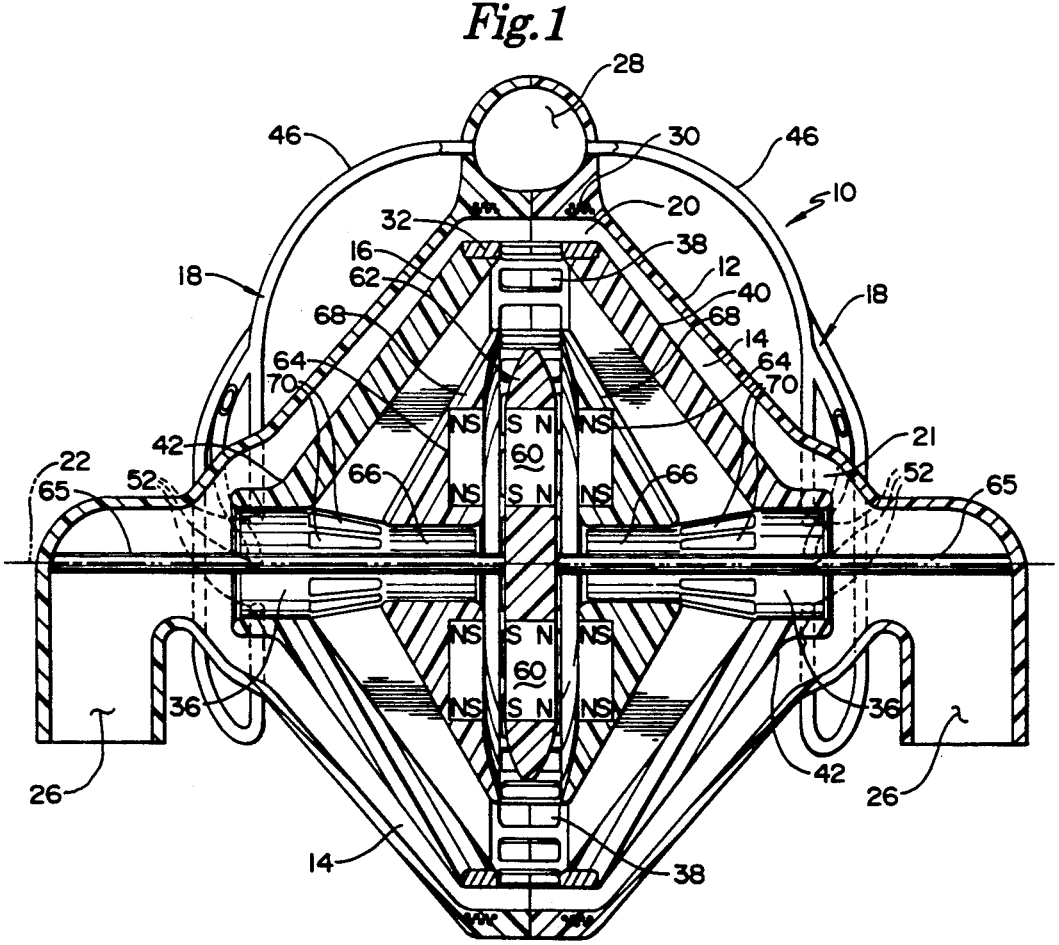

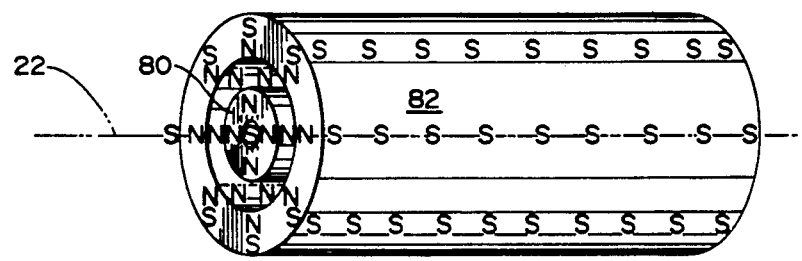
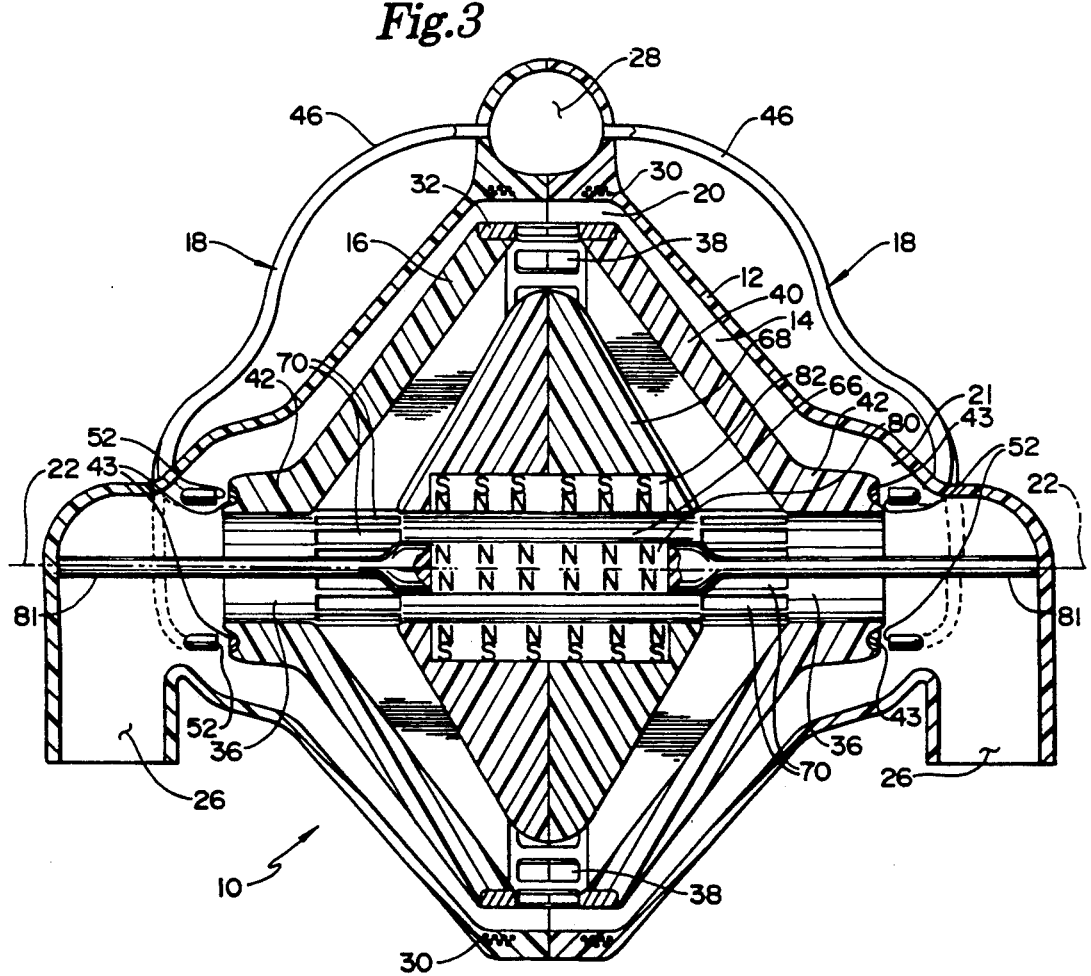

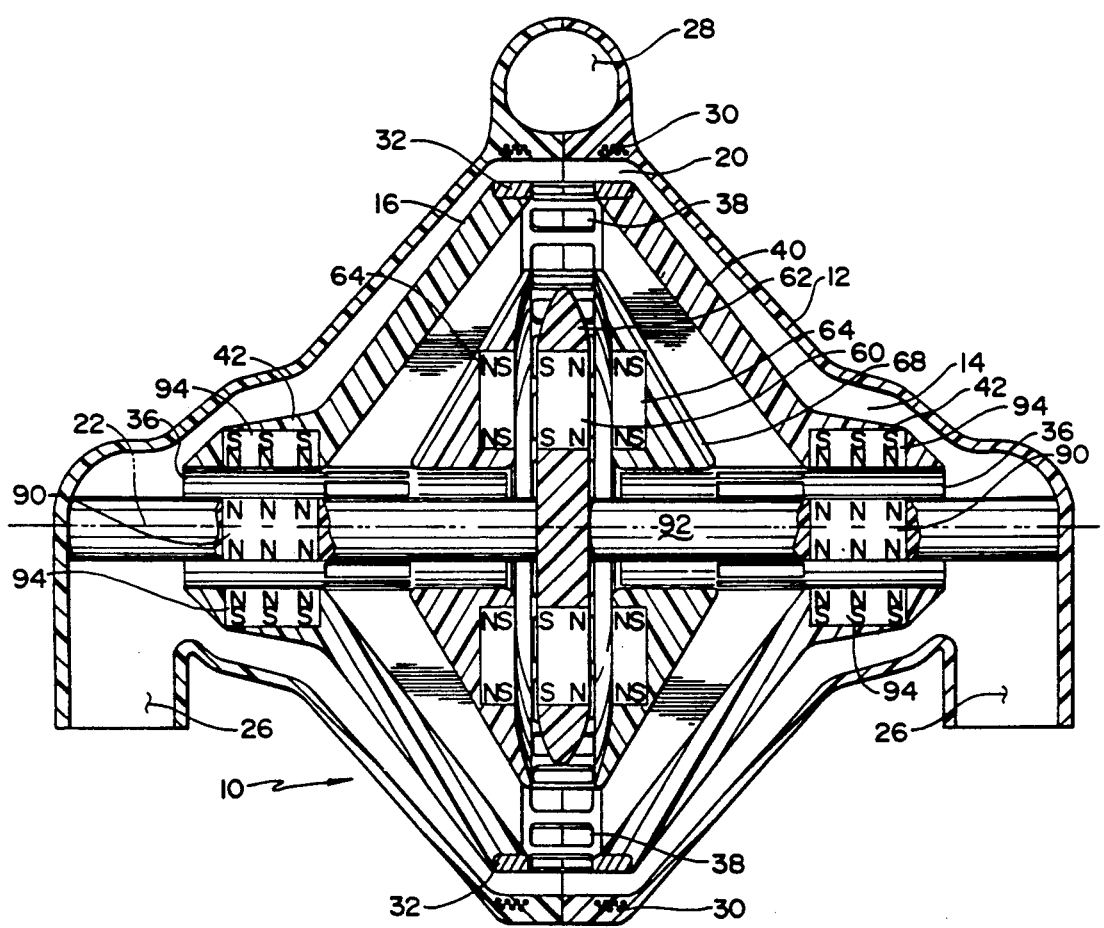

FLUID PUMP WITH MAGNETICALLY LEVITATED IMPELLER

RELATED APPLICATION

This application is a continuation-in-part of co-pending U.S. patent application Ser. No. 07/593,695, entitled Fluid Pump with Levitated Impeller, filed Oct. 5, 1990, now U.S. Pat. No. 5,055,005.

BACKGROUND OF THE INVENTION

This invention relates to a fluid pump with a rotary impeller, and more particularly to a fluid pump with a bearing-free, seal-free electromagnetically-driven rotary impeller, levitated by a combination of axial and radial localized opposed repulsive magnetic and fluid forces or by repulsive axial and radial magnetic forces only.

Levitation of the impeller by such forces allows for high efficiency in converting power into useful work. Thus, a relatively small energy source can be used and the life of the energy source is correspondingly extended. Moreover, use of a levitated impeller driven by electromagnetic forces eliminates the need for driving mechanism bearings and seals, thereby avoiding the heat build-up and leakage attendant with other rotary pump inventions. Such considerations can be of critical importance for pumping of physiological fluids such as blood.

A large number of mechanisms for pumping fluids have been described in the art, including, for example, peristaltic pumps, moving diaphragm pumps, piston-type pumps, and centrifugal or rotary pumps. Generally, a rotary pump includes a pumping chamber with inlet and outlet ports and an impeller mounted within the pumping chamber for rotation about an axis. Frequently the impeller is mounted on a shaft that extends through one or more seals and a bearing apparatus to a rotational driving mechanism outside the pumping chamber. Rotary pumps employing shaft-mounted impellers with shaft seals are exemplified in the following U.S. patents: Dorman et al. U.S. Pat. No. 3,608,088; Rafferty et al. U.S. Pat. No. 3,647,324; Reich et al. U.S. Pat. No. 4,135,253; Clausen et al. U.S. Pat. No. 4,589,822; Moise U.S. Pat. No. 4,704,121; and Kletschka U.S. Pat. No. 4,844,707. Shaft seals are susceptible to wear and heat build-up, which can lead to leakage and, in the case of blood pumps, to thrombogenic (clot-forming) problems, denaturation of proteins, and embolic phenomena and the like.

Other pump inventions employ liquid or hydrostatic bearings to reduce heat build-up and/or to dissipate heat and to reduce frictional forces in rotation of the shaft and/or impeller. In these inventions liquid or gas is forced into narrow clearances between the shaft and various bearing assemblies or between the impeller and the impeller housing. The relatively thin fluid or gas films generated in these inventions are nevertheless subject to high shear forces and some incremental heat build-up. The following U.S. patents exemplify the use of such liquid or hydrostatic bearings: Prindle U.S. Pat. Nos. 845,816 and 888,654; Anderson U.S. Pat. No. 2,864,552; Baker et al. U.S. Pat. No. 3,122,101; and Kambe et al. U.S. Pat. No. 4,475,866.

Olsen et al. U.S. Pat. No. 4,688,998 discloses a fluid pump with an electromagnetically driven and levitated impeller. In Olsen et al., a sensor and a controller is provided to sense and control the amount of electromagnetic levitating force applied to the impeller. Only electromagnetic levitating forces are applied to the impeller. Unlike the present invention, in Olsen et al. no fluid forces are available for levitation and, moreover, the electromagnetic levitated forces are not applied to the impeller in separate and distinct axial and radial directions. Consequently, a sensor and controller is necessary to adjust levitation of the impeller, which is not necessary in the present invention. While Olsen et al. eliminates the impeller drive shaft, bearings and seals, electrical power is required not only to drive the impeller but also to maintain the impeller in a suspended state. Moreover, the invention requires cooperating electromagnetic sets, sensors, suspension circuits, and sensing circuits for continuously adjusting the position of the impeller in the pump housing.

In the fluid pump disclosed in the parent application, from which this application is a continuation-in-part, while all the input energy is directed to rotation of the impeller, a portion of the input energy from the peripheral region of the impeller (which includes locations downstream from the periphery of the impeller) is diverted for use in levitating the impeller. Thus, not all of the input energy is directed toward pumping fluid. It would therefore be a significant advancement in the art to provide a novel pump apparatus whereby the impeller is levitated and positioned in the pump fluid by auto-adjusting, permanent repulsive magnetic forces and whereby it is possible for more input energy to be directed to rotation of the impeller and pumping of the fluid. Such a novel pump apparatus is disclosed and claimed herein.

SUMMARY OF THE INVENTION

In accordance with the present invention, a rotary pump is disclosed which is comprised of a housing defining a pumping chamber with one or more pumping chamber inlet ports and a pumping chamber outlet port or ports; a rotatable impeller or impellers disposed in the pumping chamber for rotation about an axis; polarized electromagnetic means for rotating the impeller about the axis; and opposed permanent magnetic means located in proximity to the impeller for levitating the impeller axially, radially or both. In the case of magnetic levitation of the impeller in the axial direction only or in the radial direction only, levitational forces in the other direction are provided by fluid forces conducted from the peripheral region downstream of the impeller. Means is provided for conducting fluid from a high pressure area at the peripheral region of the impeller and discharging the fluid in opposed directions within a lower pressure area in general proximity to the axis of the impeller, in either an axial or radial direction, thereby levitating and stabilizing the impeller within the pumping chamber by application of both axial or radial fluid forces in combination with repulsive magnetic forces in the direction (axial or radial) not supplied by the fluid forces.

The impeller may be fashioned of various materials, preferably non-magnetic such as methyl methacrylate. Preferably, the impeller has an overall bulk density similar or identical to that of the fluid being pumped, thereby resulting in suspension of the impeller in the pumped fluid and facilitating levitation and stabilization of the impeller within the pumped fluid.

The impeller may take various shapes, and may or may not have vanes, depending upon the particular pump application. The impeller may be solid, or may have internal fluid-filled space in communication with the pumping chamber or with the pumping chamber inlet and/or outlet ports. The impeller may have a single inlet or opposed inlets near the axis of the impeller communicating with the pumping chamber inlet ports, and opposed outlets at the periphery of the impeller communicating with the pumping chamber outlet port or ports. The impeller preferably has axially extending neck portions. Means for levitating the impeller comprises permanent magnets, including a centrally located magnet and a magnet or magnets surrounding the centrally located magnet spaced both axially and radially from the centrally located magnet for magnet stabilization both axially and radially, and spaced only axially or only radially for magnetic stabilization in the axial or radial direction only. In the case of magnetic stabilization in one direction (axially or radially) only, stabilizing forces in the other direction (radially or axially) are provided by conduits emanating from the vicinity of the pumping chamber outlet port and terminating in various configurations generally near the axially extending neck portion of the impeller to conduct fluid forces to the impeller for impingement on the impeller. Thus, magnetic forces, or fluid forces together with magnetic forces, cause levitation of the impeller.

Magnetic stabilization or levitation is achieved by repulsive magnetic forces in balanced opposed axial and/or radial directions as a result of centrally located magnets, fixed with respect to the housing and surrounding or bracketing magnets fixed with respect to the impeller, disposed with the polarity of the centrally located magnets and the surrounding or bracketing magnets oriented to repel. It should be noted that balanced repulsive magnetic forces are essential, as opposed to balanced attractive magnetic forces, because balanced attractive forces would cause magnetic freezing of the impeller if the impeller were to be jarred out of magnetic equilibrium because magnetic forces increase as distance decreases, thereby permanently destroying magnetic equilibrium conditions, and causing the magnets to engage and freeze the impeller in the housing.

Polarized electromagnetic means for rotating the impeller may comprise conducting wire windings within the periphery of the pump housing electromagnetically coupled to permanent magnets housed within the periphery of the impeller. Alternatively, the polarized electromagnetically means for rotating the impeller may comprise conducting wire windings housed within a stator located internal to the impeller, the stator being in structural communication with the pump housing and electromagnetically coupled to one or more magnets housed within the internal structure of the impeller.

As used herein the term "fluid" means any aggregate of matter in which the molecules are able to flow past each other without limit and without the formation of fracture planes. The term includes gases, liquids, solutions, suspensions slurries and gels and includes such specific substances as blood, plasma and serum.

BRIEF DESCRIPTION OF THE DRAWINGS

FIG. 1 is an axial sectional view of a preferred embodiment of the present invention. In FIG. 1 axial levitation of the impeller is achieved by permanent repulsive magnetic forces and radial levitation is by fluid forces.

FIG. 2 is an isolated perspective view of the permanent magnets of FIG. 1, which are used for axial levitation.

FIG. 3 is an axial sectional view of another embodiment of the present invention. In FIG. 3 radial levitation is achieved by permanent repulsive magnetic forces and axial levitation is by fluid forces.

FIG. 4 is an isolated perspective view of the permanent magnets of FIG. 3, which are used for radial levitation.

FIG. 5 is an axial sectional view of another embodiment of the present invention. In FIG. 5 both axial and radial levitation of the impeller is achieved by permanent magnetic repulsive forces.

In FIG. 7 both axial and radial levitation is achieved by both permanent repulsive magnetic forces and by fluid forces. The embodiment of FIG. 7 is thus redundant in that both magnetic and fluid forces are used to levitate the impeller both axially and radially.

DETAILED DESCRIPTION OF THE INVENTION

Figure 6:
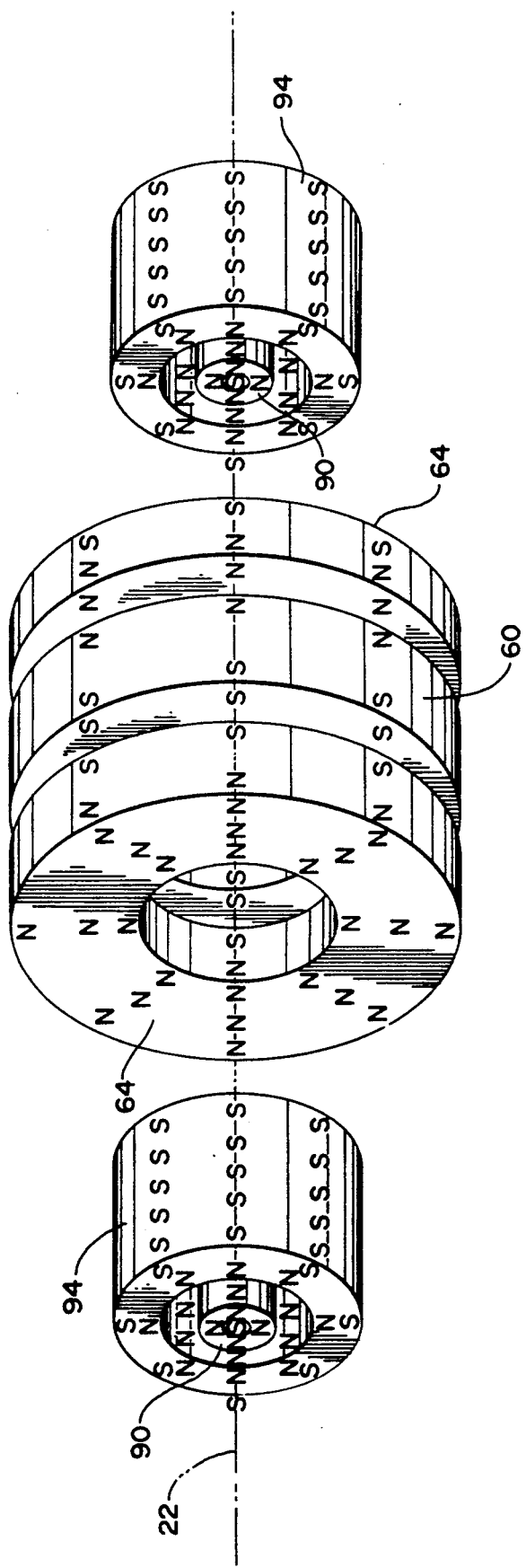
FIG. 6 is an enlarged isolated perspective view of the permanent magnets of FIG. 5, which are used for both axial and radial levitation.

FIG. 1 depicts a preferred embodiment of the pump 10 of the present invention in which axial stabilization of the impeller is achieved by repulsive magnetic forces and radial stabilization is achieved by fluid forces. The pump comprises a pump housing 12 defining a pumping chamber 14 through which fluid is pumped, an impeller 16, and means 18 for conducting fluid from a higher pressure region 20 near the periphery of the impeller, including pumping chamber outlet port 28, and discharging the fluid in a lower pressure region 21 in general proximity to the axis 22 of the impeller 16. The pump housing may be fashioned from two or more component parts secured together with fasteners. The pump housing 12 also defines pumping chamber inlet ports 26 and a pumping chamber outlet port 28. The embodiment depicted in FIG. 1 has two pumping chamber inlet ports 26 and a single pumping chamber outlet port 28. The housing 12 could be configured, however, to define a single inlet port 26 or more than two inlet ports, and/or multiple outlet ports. Other configurations of pumping chamber inlet and outlet ports for various applications of this invention will be apparent to those skilled in the art.

The periphery of the pump housing 12 incorporates electromagnetic wire windings 30 for rotating the impeller 16 about the impeller axis 22. One embodiment of the electromagnetic wire windings is shown in parent application Ser. No. 07/593,695, now U.S. Pat. No. 5,055,005. The wire windings 30 are electromagnetically coupled to permanent magnets 32 housed within and spaced about the peripheral structure of the impeller 16.

The wire windings may alternatively be incorporated into a stator located interior to the impeller 16, and about which the impeller 16 may rotate, such as shown in FIG. 20 of U.S. Pat. No. 5,055,005. The stator may be supported within the impeller by one or more supporting shafts disposed along the axis of rotation of the impeller, the shafts being in structural communication with the pump housing 12. The wire windings within the stator may be in electrical communication with one or more electrical power sources by means of wires running from the stator through the supporting shafts to one or more of such electrical power sources located within or external to the fluid pump 10. Other configurations of electromagnetic means for rotating the impeller about an axis will be obvious to those skilled in the art.

The impeller 16 has axially opposed inlets 36 communicating with the pumping chamber inlet ports 26, and opposed outlets 38 at the periphery of the impeller 16 communicating with the pumping chamber 14 and thereby with the pumping chamber outlet port 28. In operation, fluid enters the opposed inlets 36 of the impeller 16 from the pumping chamber inlet ports 26. An acceleration is imparted to the fluid due to shear forces operating between the interior walls of the rotating impeller 16 and the fluid and between the molecules and particles of the fluid. Fluid exiting the impeller outlets 38 due to centrifugal forces operating within the accelerated fluid imparts circumferentially and radially directed fluid forces to the fluid within the pumping chamber 14. Similarly directed fluid forces are generated by frictional shear forces operating between the outer surfaces 40 of the impeller 16 and the fluid and between the molecules and particles of the fluid. Fluid thus enters pump 10 at inlet ports 26 and exits at outlet port 28.

In the preferred embodiment, the impeller includes opposed, axially extending neck portions 42 that encompass the opposed inlets 36. Such neck portions facilitate radial, fluid-force levitation of the impeller by providing appropriately directed surfaces upon which levitating fluid forces may be directed. Such neck portions may be eliminated, however, by providing functionally equivalent inwardly facing surfaces for radial fluid-force levitation, such as shown in FIGS. 9, 14, 19 and 20 of U.S. Pat. No. 5,055,005, and they may be eliminated without substitution of a functional equivalent if magnetic forces are used for radial levitation. Neck portions 42 also facilitate axial, fluid-force levitation of the impeller by providing circular concave surfaces 43, shown in FIG. 3, into which the axial fluid forces may be directed. Numerous other configurations of the impeller 16, however, will be applicable to the concept embodied in the present invention — that of impeller levitation by localized forces. For examples, the total frictional force exerted by the impeller 16 on the fluid could be increased by providing additional partitions or walls within the impeller 16 transverse to the axis of rotation.

Generally, in embodiments where the invention is used for the pumping of physiological fluids such as blood, vanes and other structures potentially capable of creating turbulence and/or excessive shear forces should be avoided. However, the invention is suitable for the pumping of any fluid (liquid or gas) where the advantages of impeller levitation by localized forces are desired, and vanes and other structures designed to increase the shear forces generated by the impeller may be useful in such embodiments. In some embodiments, the fluid forces generated solely through interaction of the fluid with the rotating outer surface of the impeller may be adequate for the intended purpose(s). In such embodiments, the impeller 16 could be "solid," i.e., lacking an internal cavity in communication with the pumping chamber via impeller inlets and outlets.

For biological or medical applications, it would be useful, but not necessary, for the impeller 16 to be of a density similar or identical to that of the fluid being pumped. However, in any application and regardless of the density of the impeller 16, it is only necessary that the levitating forces be sufficient to counteract gravitational and inertial forces acting on the impeller 16. Biological and medical uses of the invention could include both human and veterinary applications. Similarly, the invention could be employed to function ex vivo (outside the body) or in vivo (inside the body), as well as in biological or non-biological and medical or non-medical uses not connected to a human or animal body.

Referring again to the preferred embodiment shown in FIG. 1, radial stabilization of impeller 16 is achieved by means 18 for conducting fluid from a region of higher fluid pressure 20 near the periphery of the impeller 16 and discharging in a region of lower fluid pressure 21 so as to radially stabilize the impeller 16 by levitating fluid forces. Means 18 is comprised of conduits 46 emanating from the pumping chamber outlet port 28. The configuration of the conduit/outlet port junction must be such that the tendency for fluid within the conduit to move toward, rather than away from, the higher pressure fluid flow region within the outlet port 28, in accordance with Bernoulli's Law, is overcome. Conduit 46 may leave the outlet port 28 at an orientation tangential to the direction of fluid flow within the outlet port in order to achieve the desired result. Alternatively, deflectors may be placed within the junction to facilitate diversion of fluid flow into the conduits 46. Other configurations of the conduit/outlet port junction for overcoming adverse fluid flow dynamics due to Bernoulli's Law will be apparent to those skilled in the art.

Referring again to the preferred embodiment shown in FIG. 1, each conduit 46 terminates in structure defining three fluid jet ports 52 within a lower fluid pressure region in the pumping chamber inlet port 26 in general proximity to the axially extending neck portion 42 of the impeller 16. The fluid jets emanating from three fluid jet ports 52 on both sides of the impeller 16 define a fluid plane or circle of orientation suitable to prevent the impeller 16 from moving in the radial direction, as shown in FIG. 1, so as not to touch the walls of the pump housing 12 or distal ends of the fluid jet ports 52. Each conduit 46 could terminate in one or more than three fluid jet ports, depending on the shape of the impeller and fluid flow dynamics in specific alternative embodiments of the invention, as shown for example in FIGS. 15-17 of U.S. Pat. No. 5,055,005.

In the configurations described above, and in alternative embodiments described below, the fluid jet ports are oriented such that the levitating fluid forces are auto-adjusting. That is, a change in corrective force will be automatically or inherently incurred by any attempted displacement in location of the impeller.

Figure 7:
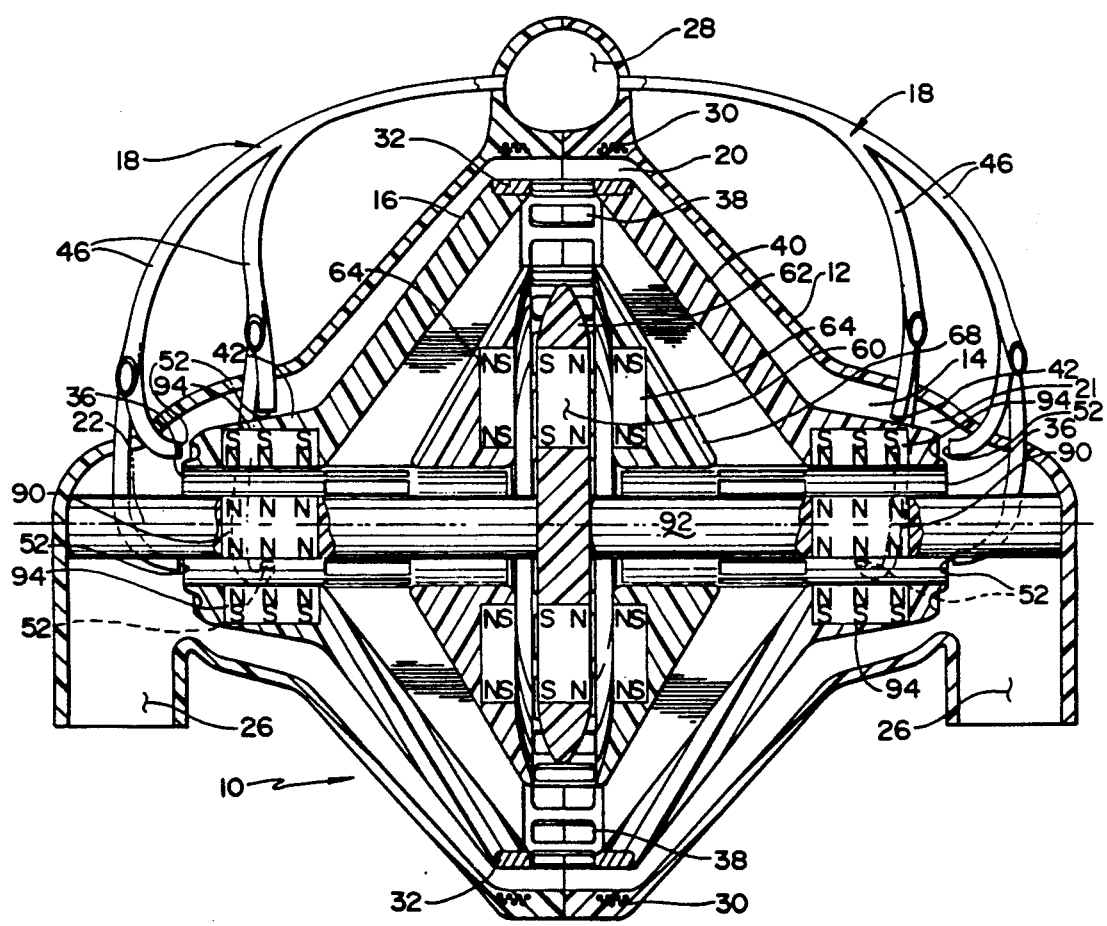
FIG. 7 is an axial sectional view of a final embodiment of the present invention.

The present invention differs from the invention of the parent application (now U.S. Pat. No. 5,055,005) in that impeller levitation is achieved by magnetic forces in addition to fluid forces or by magnetic forces alone, and is applicable to each of the embodiments shown in the patent, in addition to those disclosed herein. Magnetic forces may be used for axial stabilization, with fluid forces being used for radial stabilization, as shown in FIG. 1, magnetic forces may be used for radial stabilization with fluid forces being used for axial stabilization, as shown in FIG. 3, or magnetic forces may be used for both radial and axial stabilization, as shown in FIG. 5. In addition, both magnetic and fluid forces may be used for both radial and axial stabilization, which provides a redundancy to insure operation under various adverse conditions and greater stabilization forces under ordinary conditions, as shown in FIG. 7.

Magnetic stabilization of impeller 16 in the axial direction is shown in FIGS. 1 and 2, in which a donut-shaped, centrally-located, permanent magnet 60 is mounted in core 62, made of non-magnetic material, which is mounted to shaft 65, which is fixed at each end to housing 12 of pump 10. Centrally located magnet 60 is thus fixed with respect to housing 12 and is enveloped by impeller 16 and is, like impeller 16, disposed with its axis coincident with axis 22. Magnet 60 has a polarity as shown by lettering in FIG. 1, namely, its south pole is on the left, as viewed in FIG. 1, and its north pole is on the right.

A pair of surrounding permanent magnets 64, donut shaped and corresponding in diameter to magnet 60, as mounted on each side of magnet 60 for rotation with impeller 16. Magnets 64 thus surround or bracket magnet 60 and are disposed with their polarity opposing the polarity of magnet 60 so that magnets 60 and 64 repel one another.

It should be noted that impeller 16 is formed with an interior sleeve section 66, which serves as a mounting hub for rotor section 68, in which magnets 64 are embedded. Because of sleeve section 66, which extends to the outer surface of impeller 16, apertures 70 are provided in sleeve section 66 so fluid may pass from opposed inlets 36 of impeller 16, into the interior cavity thereof, and out impeller outlets 38. Impeller 16 could also be constructed without sleeve member 66 as long as a passage from inlet 36 to the interior cavity of impeller 16 is provided.

In the embodiment of FIGS. 1 and 2, the repulsive forces between magnets 60 and 64 thus result in axial stabilization of impeller 16 and fluid forces result in radial stabilization.

In the embodiment of FIG. 3, radial stabilization of impeller 16 is obtained by centrally located permanent magnet 80, which is axially mounted on shaft 81, which is connected to housing 12 and is thus fixed with respect to housing 12. As shown in FIGS. 3 and 4, centrally located magnet 80 is formed with a polarity such that its cylindrical surface is its north pole and its central surface as its south pole.

A surrounding cylindrical permanent magnet 82 is located concentrically about magnet 80 with its interior cylindrical surface as its north pole and its exterior cylindrical surface as its south pole. Surrounding magnet 82 is embedded in rotor 68 of non-magnetic material, which is mounted to sleeve 66 of impeller 16. Apertures 70 are provided in the embodiment of FIGS. 3 and 4 for the purpose described above in connection with the embodiment of FIGS. 1 and 2.

The repulsive magnetic forces between magnets 80 and 82 thus result in radial stabilization of impeller 16 and fluid forces result in axial stabilization.

An embodiment in which impeller stabilization in both the axial and the radial directions is by repulsive permanent magnetic forces is shown in FIGS. 5 and 6, in which axial stabilization is provided by magnets 60 and 64, which are identical to the embodiment of FIGS. 1 and 2, and radial stabilization is provided by magnets 90 and 94 in a manner similar to the embodiment of FIGS. 3 and 4, except that a pair of spaced permanent magnet sets is provided, disposed respectively at the opposed neck portions 42 of impeller 16. The two centrally located magnets 90 are mounted on shaft 92 with the exterior cylindrical surface as the north pole and the interior central surface as the south pole. The pair of cylindrical permanent magnets 94 surround each of the magnets 90 and have a south pole on the exterior cylindrical surface. The polarity of magnets 90 and 94 is therefore such that repulsive magnetic forces stabilize impeller 16 in the radial direction.

Thus, in the embodiment of FIGS. 5 and 6, impeller 16 is stabilized in both the axial and radial directions by repulsive forces between magnets 60 and 64 and magnets 90 and 94 respectively.

The embodiment shown in FIG. 7 is a combination of magnetic force stabilization in both the axial and radial directions and fluid force stabilization in both the axial and radial directions. Fluid forces are directed axially in opposed directions at each end of impeller 16 at neck portion 42 from outlet 52 of conduit 46 and, similarly, radial forces are directed in opposed directions at each end of impeller 16 at neck portion 42. Radial stabilization is also achieved by the repulsive magnetic forces between magnet 90 and 94 and axial stabilization is achieved by repulsive magnetic forces between magnets 60 and 64. The embodiment in FIG. 7 is thus redundant in that both magnetic and fluid forces combine in both the axial and radial directions. This redundancy may be of value in obtaining increased levitational or stabilizing forces and in providing a fail safe design.

Various methods may be employed to start the pumping mechanism of the present invention. The pump housing and its inlet and outlet ports, the impeller and its inlets and outlets, the conduits and fluid jet ports, and the vessels or other passageways leading to and from the pump housing may be primed with fluid prior to activation of the electromagnetic means for rotating the impeller. Fluid may be introduced into the invention at various locations from external sources. If necessary, an external pressurizing mechanism may be used to introduce an appropriate priming fluid and to expel air potentially trapped within the spaces of the invention. Once the invention has been primed, activation of the electromagnetic means may be sufficient to overcome the inertia of the impeller and to initiate rotation of the impeller. This would lead nearly immediately to generation of levitating fluid forces emanating from the fluid jet ports. As the speed of rotation of the impeller reached operating levels, the levitating fluid forces generated would bring the impeller to its operating position within the pump housing. In the case of impeller levitation in both the axial and radial directions by repulsive permanent magnetic forces, it should be recognized that levitational fluid forces generated by rotation of the impeller are not necessary.

With an impeller of a density the same as, or similar to, that of the fluid, levitating fluid forces, in the embodiments of FIGS. 1-4, will bring the impeller to its operating position very shortly after the activated electromagnetic means has induced the first several rotations of the impeller. In any case, structural constraints on displacement of the impeller from its operating position within the housing may be incorporated by those skilled in the art. For example, the spacing between the conduit jet port structure and the impeller should be less than the spacing between the impeller and that portion of the housing encompassing the electromagnetic wire windings. Such structural constraints as described above, as well as others known to those skilled in the art, would facilitate starting of the pumping mechanism in those embodiments reliant upon fluid forces for impeller stabilization, since the impeller driving magnets would not be in a "freeze-up" contact with the electromagnetic wire windings at start-up, and movement of the impeller from its start-up position to its operating position would entail only a slight positional reorientation.

In certain application, such as pumping human or animal blood, the surfaces of the impeller, the structure comprising the fluid jet ports, and, if present, the arresting surfaces, should be manufactured of smooth, non-magnetic materials having low coefficients of friction and low or non-thrombogenic characteristics.

The preferred application of pumps of the present invention is in the medical field for the pumping of blood, although the invention may be used in numerous other medical and non-medical pumping applications. In human medicine, it is unknown whether or not a pulsatile blood flow is required for optimum short-term or long-term clinical efficacy of artificial blood pumps. The rotary impeller 16 of the present invention is most conveniently operated in a continuous, non-pulsatile mode. However, depending on the configuration and mode of operation of the electromagnetic means for driving the impeller 16, the mode of operation may be pulsatile, or even intermittent. Likewise, the levitating fluid jets could be operated in a continuous, pulsatile, or intermittent mode. Alternatively, the operation of the impeller and levitating fluid jets could fluctuate between continuous, pulsatile, and intermittent modes, or between any combination of these modes, depending on the structure and intended use of specific embodiments of the present invention. Appropriate modes of operation will be obvious to those skilled in the art.

From the foregoing, it will be obvious to those skilled in the art that various modifications in the above described devices can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for stabilizing the position of a rotatable impeller suspended in fluid in a pumping chamber, the impeller having an axis of rotation, the pumping chamber having a pumping chamber inlet port and a pumping chamber outlet port, which comprises: the step of suspending the impeller in the fluid in the pumping chamber by repulsive permanent magnetic forces directed in opposed axial directions toward the impeller, and the additional step of conducting fluid from the periphery of the impeller and discharging the fluid in the pumping chamber in opposed radial directions toward the impeller, to thereby stabilize the impeller axially by levitating magnetic forces and radially by levitating fluid forces.

2. A method for stabilizing the position of a rotatable impeller suspended in fluid in a pumping chamber, the impeller having an axis of rotation, the pumping chamber having a pumping chamber inlet port and a pumping chamber outlet port, which comprises: the step of suspending the impeller in the fluid in the pumping chamber by repulsive permanent magnetic forces directed in opposed radial directions toward the impeller, and the additional step of conducting fluid from the periphery of the impeller and discharging the fluid in the pumping chamber in opposed axial directions toward the impeller, to thereby stabilize the impeller radially by levitating magnetic forces and axially by levitating fluid forces.

3. A method for stabilizing the position of a rotatable impeller suspended in fluid in a pumping chamber, the impeller having an axis of rotation, the pumping chamber having a pumping chamber inlet port and a pumping chamber outlet port, which comprises: the step of suspending the impeller in the fluid in the pumping chamber by repulsive permanent magnetic forces directed in opposed axial and radial direction toward the impeller, and the additional step of conducting fluid from the periphery of the impeller and discharging the fluid in the pumping chamber in opposed axial and radial directions toward the impeller, to thereby stabilize the impeller both axially and radially by both magnetic and fluid levitating forces.

4. A fluid pump comprising:
   a. a housing defining a pumping chamber, a pumping chamber inlet port and a pumping chamber outlet port;
   b. a rotatable impeller disposed in the pumping chamber for rotation about an axis, wherein the impeller has opposed inlets in general proximity to the axis of the impeller communicating with the pumping chamber inlet port, and opposed outlets at the periphery of the impeller radially spaced from the inlets, and includes opposed axially extending neck portions, the proximal portion of each said neck portion being attached to, and centered on, a central axial surface of the impeller, and the distal end of each said neck portion being housed in proximity to the corresponding adjacent pumping chamber inlet port;
   c. polarized electromagnetic means for rotating the impeller about the axis;
   d. a centrally-located, permanent magnet fixed axially with respect to the housing;
   e. a surrounding permanent magnet disposed about the centrally located magnet and fixed with respect to the impeller; and
   f. means for conducting fluid from the peripheral region of the impeller and discharging the fluid in opposed radial directions toward the impeller, to thereby levitate the impeller in the housing axially by levitating magnetic forces and radially by levitating fluid forces.

5. A fluid pump comprising:
   a. a housing defining a pumping chamber, a pumping chamber inlet port and a pumping chamber outlet port;
   b. a rotatable impeller disposed in the pumping chamber for rotation about an axis, wherein the impeller has opposed inlets in general proximity to the axis of the impeller communicating with the pumping chamber inlet port, and opposed outlets at the periphery of the impeller radially spaced from the inlets, and includes opposed axially extending neck portions, the proximal portion of each said neck portion being attached to, and centered on, a central axial surface of the impeller, and the distal end of each said neck portion being housed in proximity to the corresponding adjacent pumping chamber inlet port;

c. polarized electromagnetic means for rotating the impeller about the axis;

d. a centrally-located, permanent magnet fixed radially with respect to the housing;

e. a surrounding permanent magnet disposed about the centrally located magnet and fixed with respect to the impeller; and f. means for conducting fluid from the peripheral region of the impeller and discharging the fluid in opposed axial directions toward the impeller, to thereby levitate the impeller in the housing radially by levitating magnetic forces and axially by levitating fluid forces.

6. The fluid pump of claim 4 or 5, wherein said means for conducting fluid from the peripheral region of the impeller and discharging the fluid toward the impeller so as to stabilize the impeller by levitating fluid forces is comprised of conduits emanating from the periphery of the impeller, each said conduit terminating in structure defining one or more fluid jet ports within the region of the pumping chamber inlet port in proximity to and directed toward the axially extending neck portion of the impeller.

7. The fluid pump of claim 4, wherein said means for conducting fluid from the peripheral region of the impeller and discharging the fluid in opposed radial directions toward the impeller is disposed to direct fluid radially toward said axially extending neck portions.

8. The fluid pump of claim 5, wherein said axially extending neck portions of said impeller include an axially-facing, circular concave surface and said means for conducting fluid from the peripheral region of the impeller and discharging the fluid in opposed axial directions toward the impeller is disposed to direct fluid into said concave surface.

9. A fluid pump comprising:

a. a housing defining a pumping chamber, a pumping chamber inlet port and a pumping chamber outlet port;

b. a rotatable impeller disposed in the pumping chamber for rotation about an axis;

c. polarized electromagnetic means for rotating the impeller about the axis;

d. a first centrally-located, permanent magnet axially fixed with respect to the housing;

e. a first pair of revolving permanent magnets axially fixed with respect to the impeller and disposed about the first centrally-located, permanent magnet, with the polarity of the first centrally-located magnet and the polarity of the first pair of revolving permanent magnets juxtaposed to produce repulsive magnetic forces, to thereby stabilize the impeller axially by levitating magnetic forces;

f. a second centrally-located permanent magnet radially fixed with respect to the housing; and g. a second pair of revolving permanent magnets radially fixed with respect to the impeller and disposed about the second centrally-located permanent magnet, with the polarity of the second centrally-located magnet and the polarity of the second pair of revolving magnets juxtaposed to produce repulsive magnetic forces, to thereby stabilize the impeller radially by levitating magnetic forces.

10. The fluid pump of claim 9, wherein the density of the impeller is similar to that of the fluid.

11. The fluid pump of claim 9, wherein the impeller has opposed inlets in general proximity to the axis of the impeller, communicating with the pumping chamber inlet port, and opposed outlets at the periphery of the impeller radially spaced from the opposed inlets.

12. The fluid pump of claim 11, and means for conducting fluid from the peripheral region of the impeller and discharging the fluid in opposed radial directions toward the impeller, to thereby stabilize the impeller radially by both magnetic and fluid levitating forces.

13. The fluid pump of claim 11, and means for conducting fluid from the peripheral region of the impeller and discharging the fluid in opposed axial directions toward the impeller to thereby stabilize the impeller axially by both magnetic and fluid levitating forces.

14. The fluid pump of claim 13, and means for conducting fluid from the peripheral region of the impeller and discharging the fluid in opposed axial direction toward the impeller, to thereby stabilize the impeller both axially and radially by both magnetic and fluid levitating forces.

* * * * *